(12) United States Patent
Akiyama et al.

(10) Patent No.: US 6,878,339 B2
(45) Date of Patent: Apr. 12, 2005

(54) NOX-CONCENTRATION MEASURING APPARATUS

(75) Inventors: Shigeyuki Akiyama, Kyoto (JP); Satoshi Inoue, Kyoto (JP); Masahiko Fujiwara, Kyoto (JP)

(73) Assignee: Horiba, Ltd., Kyoto (JP)

( * ) Notice: Subject to any disclaimer, the term of this patent is extended or adjusted under 35 U.S.C. 154(b) by 235 days.

(21) Appl. No.: 10/367,685

(22) Filed: Feb. 19, 2003

(65) Prior Publication Data

US 2003/0156982 A1 Aug. 21, 2003

(30) Foreign Application Priority Data

Feb. 19, 2002 (JP) ........................................ 2002-041100

(51) Int. Cl.⁷ ................................................. G01N 1/22
(52) U.S. Cl. .................. 422/62; 422/83; 436/116; 436/117; 436/118; 436/175; 436/181
(58) Field of Search ............................. 422/62, 83, 88, 422/91, 93; 436/52, 116, 117, 118, 175, 181

(56) References Cited

U.S. PATENT DOCUMENTS

| 3,904,739 A | * | 9/1975 | Uehara et al. .............. 423/400 |
| 3,917,454 A | * | 11/1975 | Clark ....................... 73/863.11 |
| 3,970,430 A | * | 7/1976 | Reader et al. .............. 436/116 |
| 4,042,333 A | * | 8/1977 | Dell et al. .................. 436/116 |
| 4,154,579 A | * | 5/1979 | Kreisel ....................... 436/168 |
| 4,197,177 A | * | 4/1980 | Proctor ....................... 204/409 |
| 5,314,828 A | * | 5/1994 | Dalla Betta et al. ........ 436/118 |
| 5,571,724 A | * | 11/1996 | Johnson ....................... 436/116 |
| 5,846,831 A | * | 12/1998 | Silvis ........................... 436/55 |
| 6,143,245 A | * | 11/2000 | Yan et al. ...................... 422/52 |

FOREIGN PATENT DOCUMENTS

JP         6-123682          5/1994

OTHER PUBLICATIONS

Japanese Industrial Standard (JIS B 7982–1995), Continuous Analyzers For Oxides Of Nitrogen In Flue Gas, Japanese Standards Association.

* cited by examiner

Primary Examiner—Jeffrey R. Snay
(74) Attorney, Agent, or Firm—Sughrue Mion, PLLC

(57) ABSTRACT

The present invention provides a NOx-concentration measuring apparatus D for quantitatively analyzing the concentration of NOx contained in a sample gas. The measuring apparatus D comprises a sampling probe for obtaining the sample gas, a drain separator 2 for condensing moisture contained in the sample gas as a condensed water and separating the condensed water from the sample gas, an $NO_2$ converter 3 for converting $NO_2$ contained in the sample gas into NO, a secondary cooling device 7 for additionally cooling the sample gas, and an NO analyzer 1, arranged in this order with respect to a sample-gas line of the NOx-concentration measuring apparatus. The drain separator is a high-flow-velocity cooling type drain separator.

Further, the sample-gas line between the sampling probe and the drain separator is heated and/or thermally insulated over the entire length thereof. The measuring apparatus can provide a high-precision measurement while suppressing $NO_2$ loss.

6 Claims, 7 Drawing Sheets

FIG. 3

Comparison of Respective NO$_2$ Losses(%) in Different Drain Separators

| a1 Vortex cooling tube type | a2 Vortex cooling tube type | b. glass funnel type | c. PVC cylinder type |
|---|---|---|---|
| 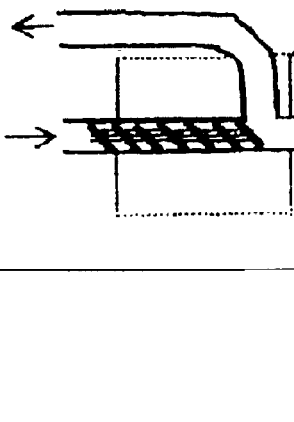 Heat Exchanging Block<br>The flow rate at water condenced point is high | 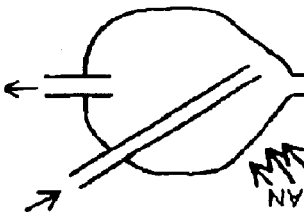 Heat Exchanging Block<br>The flow rate at water condenced point is high | 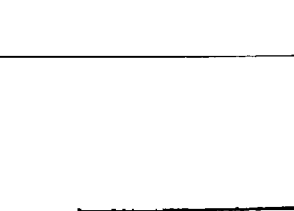<br>Improvement of heat conduction, but easily broken | 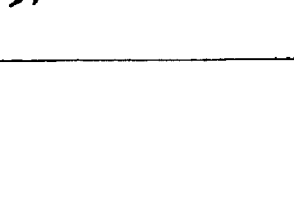<br>Adhesion of condenced water is not small, retension of condenced water on the bottom is not small |
| Internal Volume 5.6cm$^3$ | Internal Volume 11cm$^3$ | Internal Volume 270cm$^3$ | Internal Volume 320cm$^3$ |
| Internal Area 38cm$^2$ | Internal Area 50cm$^2$ | Internal Area 200cm$^2$ | Internal Area 280cm$^2$ |
| NO$_2$ loss 0.46% | NO$_2$ loss 1.20% | NO$_2$ loss 2.09% | NO$_2$ loss 3.42% |

NOX-CONCENTRATION MEASURING APPARATUS

FIELD OF THE INVENTION

The present invention relates to a NOx-concentration measuring apparatus used for measuring the concentration of nitrogen oxides (NOx) contained in emission gas from a flue, gas duct or the like.

DESCRIPTION OF THE PRIOR ART

For combustion control in thermal power plants, it is essential, in terms of environmental protection, to suppress the generation of nitrogen oxides (NOx) and to reduce the concentration of unreacted leak ammonia after de-nitration reaction, and it is also essential, in terms of energy saving, to control the injection amount of ammonia for optimizing a denitration process. For this purpose, it is required to measure the concentration of NOx in an emission or flue gas sample taken from a flue. A NOx-concentration measuring apparatus is used in such measurements.

Among NOx contained in the flue gas, nitrogen monoxide (NO), due to its stable physicochemical properties, is seldom adsorbed onto the inner wall of pipes of the NOx-concentration measuring apparatus or seldom dissolved in a condensed water, which is likely to be formed in the NOx-concentration measuring apparatus. In contract, nitrogen dioxide ($NO_2$) is inherently apt to cause the above-adsorption or dissolution. However, the requirement for controlling the concentration of $NO_2$ has not been so strict because NOx in emission gas from a flue or the like generally comprise a large percent of NO and only several percent (5 to 10%) of $NO_2$. Consequently, the measurement error of $NO_2$ concentration has been a minor concern, and even the factor causing such an error has not been elucidated.

In late years, an LNG-combined composite power plant, based on a high-temperature combustion using LNG (liquid natural gas) valued as one of clean fuels, has been increasingly constructed and operated, and advanced plant technologies of denitration have been concurrently developed. Under these circumstances, the ratio of $NO_2$ to the entire NOx in the flue gas has been increased up to 50% or more in many cases, and thereby the measurement error of $NO_2$ concentration has become a non-negligible issue.

The inventors have studied the causes of error in measurement of $NO_2$ concentration and found the following two major factors: (1) $NO_2$ loss arising from adsorption of $NO_2$ onto the inner wall of pipes and/or devices constituting a sampling system; and (2) $NO_2$ loss arising not only from the dissolution of $NO_2$ into a condensed water at an undesirable (unintended) position of the sampling system, but also from the deterioration in the conversion efficiency of an $NO_2$ converter for converting $NO_2$ into NO, caused by condensed water, micro-dusts, $NH_3$ or the like mixed in the $NO_2$ converter. Based on these findings, the inventors have accomplished an improved NOx-concentration measuring apparatus capable of suppressing the $NO_2$ loss otherwise arising from the above two causes.

Japanese Patent Laid-Open Publication No. 6-123628 discloses a NOx-concentration measuring apparatus capable of continuously measuring NOx concentration in emission gas, even in the case where the $NO_2$ ratio is high. This Patent Publication also discloses a sampling device capable of preventing the dissolution of $NO_2$ to provide enhanced analytical accuracy.

In the NOx-concentration measuring apparatus disclosed in the above Patent Publication, a gas sample taken by a sampling probe is introduced into a first NOx converter through a duct having an anti-condensed water-forming measure for thermally insulating the duct, and then introduced in a dehumidifier through a duct having a molybdenum (Mo) heat coil loaded therein, so that moisture in the sample gas is removed by the dehumidifier. That is, this apparatus is intended to suppress the $NO_2$ loss arising from the above cause (2). However, in order to supply the demands for the accuracy of a low NOx concentration, the sample gas to be taken from a flue contains ammonia used in denitration (NOx removal) equipment to reduce NOx concentration in a flue gas. Thus, in the NOx-concentration measuring apparatus disclosed in the above Patent Publication, the first NOx converter located on an upstream side of the dehumidifier can be disadvantageously poisoned by the ammonia, resulting in significantly deteriorated converter efficiency.

A sampling device disclosed in Japanese Registered Utility Model Publication No. 2587823 comprises a sampling line including three-stage dehumidification means for effectively preventing the formation of condensed water in the sampling line. This device is intended to suppress the $NO_2$ loss arising from the above case (2) but not to suppress the $NO_2$ loss arising from the above cause (1).

SUMMARY OF THE INVENTION

In view of the above circumstances, it is therefore an object of the present invention to provide a NOx-concentration measuring apparatus capable of suppressing $NO_2$ loss due to adsorption and/or dissolution of $NO_2$, thereby accomplishing a high-precision measurement.

In order to achieve this object, the present invention provides a NOx-concentration measuring apparatus for quantitatively analyzing the concentration of NOx contained in a sample gas. This measuring apparatus comprises a sampling probe for obtaining the sample gas, a drain separator for condensing moisture contained in the sample gas as a condensed water and separating the condensed water from the sample gas, an $NO_2$ converter for converting $NO_2$ contained in the sample gas into NO, a secondary cooling device for additionally cooling the sample gas, and an NO analyzer, arranged in above stated with respect to a sample-gas line of the NOx-concentration measuring apparatus. The drain separator is a high-flow-velocity cooling type drain separator. Further, the sample-gas line between the sampling probe and the drain separator is heated and/or thermally insulated over the entire length thereof.

The NOx-concentration measuring apparatus constructed as above can suppress $NO_2$ loss due to adsorption and/or dissolution of $NO_2$ to provide a high-precision measurement.

A ratio of the flow rate of the sample gas passing through the drain separator to the internal volume of the drain separator and/or a ratio of the flow rate of the sample gas passing through the drain separator to the internal surface area of a sample-gas passage formed in the drain separator can be increased in a desirable range.

More specifically, the ratio of the flow rate ($cm^3$/min) of the sample gas passing through the drain separator to the internal volume ($cm^3$) of the drain separator can be set at 10 ($min^{-1}$) or more, and/or the ratio of the flow rate ($cm^3$/min) of the sample gas passing through the drain separator to the internal surface area ($cm^2$) of the sample-gas passage can be set at 15 (cm/min) or more.

In the NOx-concentration measuring apparatus of the present invention, the drain separator and the secondary cooling device may be incorporated in a single unit. In this case, the apparatus is advantageously simplified and downsized in structure, in addition to the above advantage.

BRIEF DESCRIPTION OF THE DRAWINGS

FIG. 3 is a schematic explanatory diagram showing conventional drain separators used in a comparative experimental test to the drain separator in the first embodiment;

DESCRIPTION OF THE PREFERRED EMBODIMENT

With reference to the drawings, embodiments of the present invention will now be described.

Figure 1:
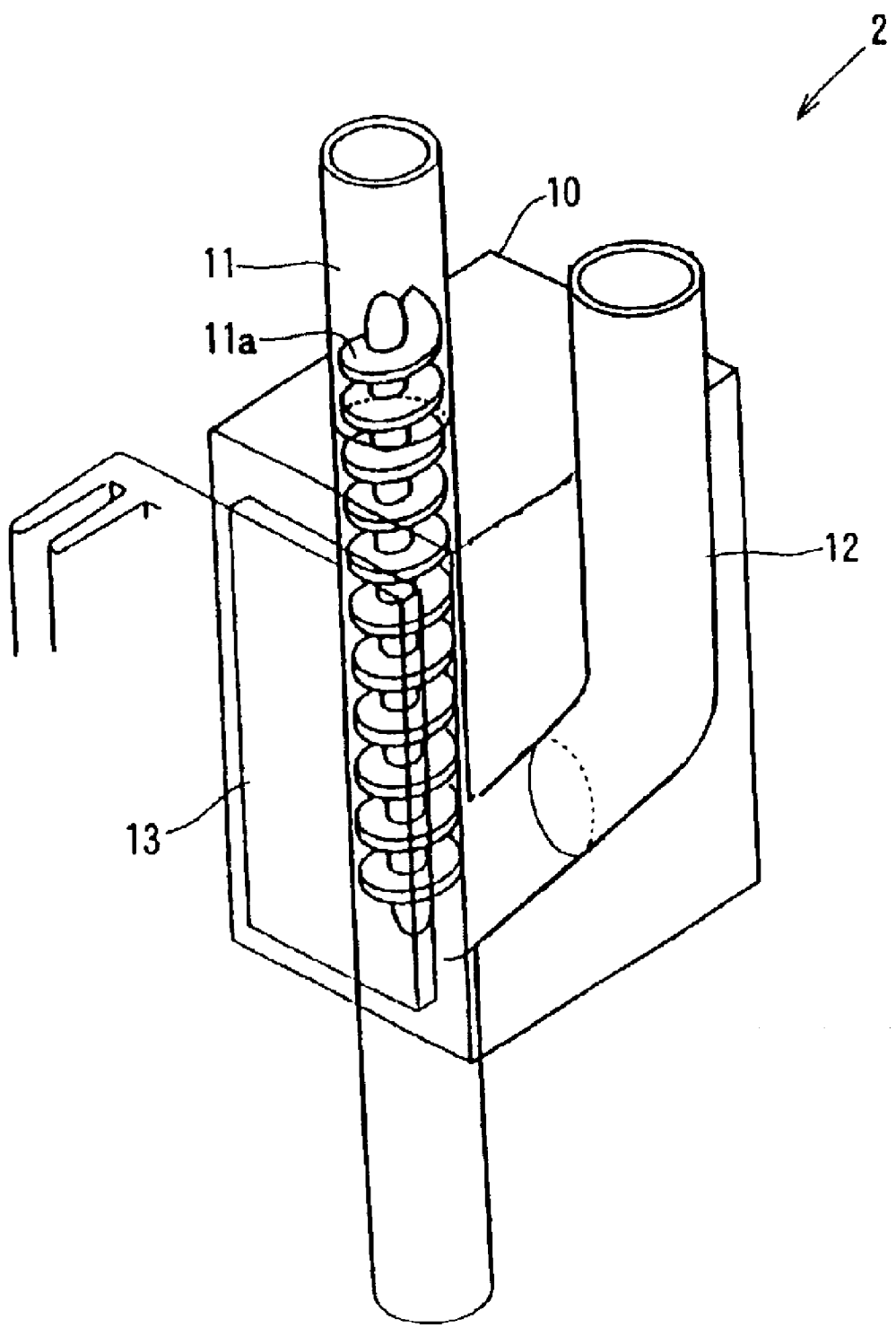
FIG. 1 is a schematic explanatory block diagram showing a NOx-concentration measuring apparatus according to a first embodiment of the present invention.

FIG. 1 is a schematic explanatory block diagram showing a NOx-concentration measuring apparatus (hereinafter referred to as "measuring apparatus" for brevity) D according to a first embodiment of the present invention.

The measuring apparatus D, operable to quantitatively analyze the concentration of NOx contained in a sample gas, comprises a sampling line L for providing fluid communication between a sampling probe 21 for obtaining the sample gas and an NO analyzer 1. Along the sampling line L, the measuring apparatus D further includes a drain separator 2 for condensing the moisture in the sample gas as a condensed water and separating the condensed water from the sample gas, an $NO_2$ converter 3 for converting $NO_2$ contained in the sample gas into NO, a filter 4 for removing a dust contained in the sample gas, a control valve 5 for adjusting the flow volume or flow rate of the sample gas to be passed through the sampling line L, a gas suction pump 6 for making a sample-gas flow from the sampling probe 21 to the NO analyzer, a secondary cooling device 7 for additionally cooling the sample gas to be introduced into the NO analyzer 1, arranged in this order from the upstream side of the sampling line L.

The sampling line L of the measuring apparatus D includes an introduction line La for providing fluid communication between the sampling probe 21 and the drain separator 2. The introduction line La is configured to be heated and/or thermally insulated over the entire length thereof. In this illustrative embodiment, the introduction line La is composed of an upstream portion formed as a heated pipe 8 having heating means such as a heater (not shown), and a downstream portion formed as a hot hose 9 made of a material having an excellent thermal insulation property. For example, the length of the heated pipe 8 may be about 50 m, and the length of the hot hose 9 may be about 1 to 5 m.

The sample probe 21 allows a part of a flue gas G flowing through a flue 22 to be picked up as the sample gas. For this purpose, the sample probe 21 may include a sampling probe 21 inserted into the flue 22 within which the flue gas G flows.

Figure 2:
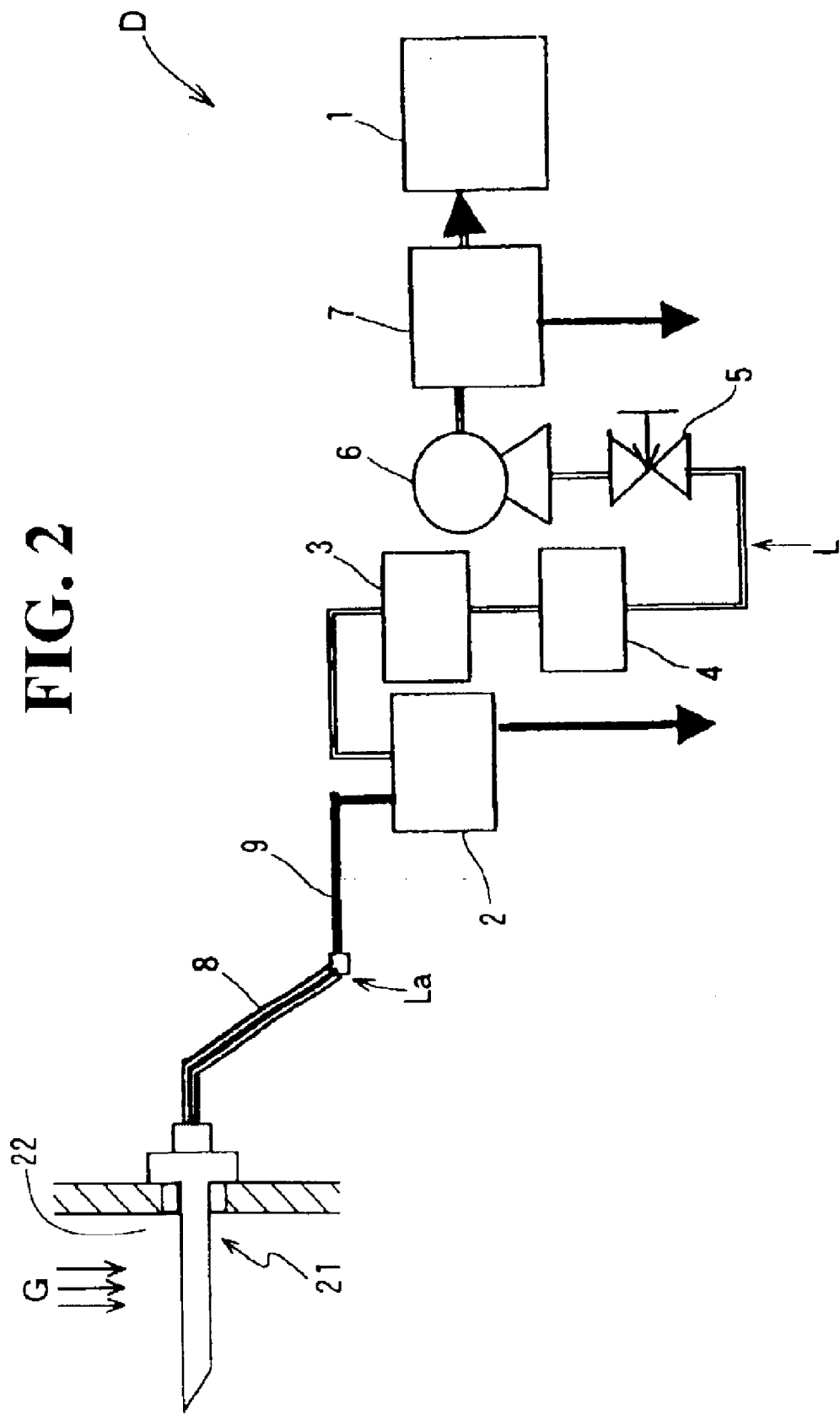
FIG. 2 is a schematic fragmentary perspective view showing a drain separator in the first embodiment.

The drain separator 2 is the so-called high-flow-velocity cooling type drain separator capable of cooling the sample gas passing therethrough at a high flow velocity. As shown in FIG. 2, the drain separator 2 comprises a block 10 made of a metal having a high thermal conductivity, a heat exchange pipe 11 extending penetratingly through the block 10 approximately vertically, a branch passage 12 branched from the heat exchange pipe 11 to extend obliquely upward, and cooling means 13 for cooling the block 10.

The block 10 may be formed in an approximately rectangular parallelepiped or cubic shape.

The heat exchange pipe 11 has an approximately circular cross-section, and includes a spiral-channel forming member 11a for forming a spiral channel mainly in a portion of the heat exchange pipe 11 located inside the block 10. The spiral-channel forming member 11a may also be made of a metal having a high thermal conductivity.

The branch passage 12 is branched from the lower portion of the heat exchange pipe 11 located inside the block 10.

The cooling means 13 is fixed onto and along one of the side surfaces of the block 10. The cooling means 13 may be formed by use of a thermoelectric-cooling Peltier element (Peltier cooling element). Further, the heat exchange pipe 11 is disposed close to the side surface of the block 10 to which the cooling means 13 fixed.

According to the drain separator 2 constructed as above, a sample gas introduced in the drain separator 2 from its upper side is cooled down while passing through the heat exchange pipe 11 downward. A resultingly condensed water continues to flow downward through the heat exchange pipe 11 separately from the sample gas, and the sample gas separated from the condensed water will flow through the branch passage 12 to the $NO_2$ converter 3 by the suction force of the gas suction pump 6.

The sample gas is most effectively cooled when it passes through the spiral channel formed between the inner wall of the heat exchange pipe 11 and the spiral-channel forming member 11a. In addition, the sample gas passes through the spiral channel at a high flow velocity because the spiral channel has a smaller cross-section than that of another portion of the heat exchange pipe 11. As above, one of the primary characteristics of the drain separator 2 in this embodiment is the provision of the spiral channel that fulfills its function of condensing the moisture in the sample gas as a condensed water and separating the condensed water from a sample gas.

The control valve 5 may be composed of a needle valve.

The second cooling device 7 may be an electronic condenser or cooler. Further, the secondary cooling device 7 may employ the same structure as that of the drain separator 2.

The measuring apparatus D constructed as above will be operated as follows.

A sample gas taken from the sampling probe 21 first passes through the introduction line La. If the moisture contained in the sample gas is condensed as a condensed water in the introduction line La, $NO_2$ will be dissolved in the condensed water, resulting in the $NO_2$ loss. Thus, it is required to heat and/or thermally insulate the introduction line La over its entire length to the extent that condensation of condensed water cannot be formed. On the other hand, it is preferable to lower the temperature of the sample gas to be introduced into the drain separator 2 located immediately on the downstream side of the introduction line La as much as possible, because the sample gas having an unduly high temperature leads to excessively increased thermal load on the drain separator 2.

For example, the downstream end of the hot hose 9 or in the vicinity of an inlet of the drain separator 2 can be set to have a temperature of 55° C. or more (equal to or higher than the dew point of moisture in the sample gas, for example 65° C.) by controlling the temperature of the heated pipe 8 in fluid communication with the drain separator 2 through the hot hose 9 and thermally insulating the hot hose 9. Alternatively, the hot hose 9 itself may be controlled to have a temperature of 55° C. or more. The above structure allows the introduction line La to be heated up to and/or thermally insulated at an adequate temperature. This prevents the sample gas flowing through the introduction line La from cooling down to an excessively low temperature, thereby avoiding the condensation of moisture contained in the sample gas or the formation of condensed water. In addition, since the drain separator 2 can be supplied with the sample gas having an adequately lowered temperature, it is possible to reduce the thermal load on the drain separator 2.

For example, the temperature of the inlet of the drain separator 2 can be set at 65° C. by controlling the temperature of the heated pipe 8 to be several-ten degrees higher than the temperature of the inlet of the drain separator 2 (e.g., to be about 80 to 100° C.). If the temperature of the inlet of the drain separator 2 cannot be sufficiently raised by heating only the heated pipe 8, the hot hose 9 may additionally be heated.

After passing through the introduction line La, the sample gas having the controlled temperature of about 65° C. is supplied to the drain separator 2, where the moisture contained in the sample gas is condensed to form a condensed water, and the condensed water will be separated from the sample gas. The sample gas getting out of the drain separator 2 has a temperature (e.g. a temperature being about 5° C. lower than room temperature) which causes no condensed water to be formed in the measuring apparatus (in the sampling line). This sample gas is then introduced into the $NO_2$ converter 3, where $NO_2$ contained in the sample gas will be converted into NO.

Subsequently, the sample gas passes through the filter 4 for removing dusts in the sample gas and the secondary cooling device 7 for additionally cooling the sample gas, and then enters into the NO analyzer 1. The measuring apparatus D is configured such that the sample gas immediately after getting out of the secondary cooling device 7 has a temperature of about 2.5 to 5° C.

In the measuring apparatus D constructed as above, by heating and/or thermally insulating the upstream side of the drain separator 2, i.e., the introduction line La, between the sampling probe 21 and the drain separator 2, it is possible to prevent the moisture in the sample gas from being condensed as a condensed water in the pipes and to prevent $NO_2$ in the sample gas from being adsorbed onto the inner wall of the pipes. That is, the measuring apparatus D can prevent the moisture in the sample gas from being condensed as a condensed water at any undesirable (unintended) position other than the drain separator 2, which condenses the moisture in the sample gas as a condensed water and separates the condensed water from the sample gas, thereby allowing the moisture in the sample gas to be condensed and separated predominantly or concentratedly at the drain separator 2. Thus, as contrast to the conventional apparatuses in which the condensed water is formed in wide-ranging undesirable (unintended) positions, the measuring apparatus D can reduce the $NO_2$ loss and achieve a high-precision measurement.

In addition, since the moisture in the sample gas taken by the sampling probe 21 is condensed and separated from the sample gas on the upstream side of the $NO_2$ converter 3, it is possible to prevent the condensed water, $NH_3$ or the like contained in the sample gas deteriorating a catalyst of the $NO_2$ converter 3, thereby suppressing deterioration in the conversion efficiency of the $NO_2$ converter 3. This advantage also contributes to minimization of the $NO_2$ loss and achievement of the high-precision measurement.

Furthermore, the drain separator 2 used in the measuring apparatus D is a high-flow-velocity cooling type drain separator which is designed to increase the flow velocity or flow rate of a gas (sample gas) passing through the drain separator, as compared to commonly used drain separators, in order to allow $NO_2$ in the sample gas to be minimally dissolved in the condensed water. Specifically, the drain separator 2 is designed to increase both a ratio of the flow rate of the sample gas passing through the drain separator 2 to the internal volume of the drain separator 2 (the flow rate of the sample gas passing through the drain separator 2/the internal volume of the drain separator 2) and a ratio of the flow rate of the sample gas passing through the drain separator 2 to the internal surface area (gas contact area or area contacting the sample gas) of a sample gas passage formed in the drain separator 2 (the flow rate of the sample gas passing through the drain separator 2/the internal surface area of a sample gas passage formed in the drain separator 2). More specifically, the drain separator 2 is designed such that the ratio of the flow rate ($cm^3$/min) of the sample gas passing through the drain separator 2 to the internal volume ($cm^3$) of the drain separator 2 is 10 ($min^{-1}$) or more, and the ratio of the flow rate ($cm^3$/min) of the sample gas passing through the drain separator 2 to the internal surface area ($cm^2$) of a sample gas passage formed in the drain separator 2 is 15 (cm/min) or more.

The $NO_2$ loss, caused by adsorption of $NO_2$ onto the inner wall of pipes or the inside of devices (drain separator 2 in this embodiment) constituting a sampling system, can be reduced by using the aforementioned high-flow-velocity cooling type drain separator 2. In order to demonstrate this advantage, an experimental test was performed by comparing the respective $NO_2$ losses (%) in drain separators a1, a2 having a structure equivalent to that of the drain separator 2 according to this embodiment and two types of conventional drain separators b, c.

Both the drain separators a1, a2 are equally the high-flow-velocity cooling type drain separator having the structure as shown in FIG. 2. The drain separator a1 has an internal volume of 5.6 ($cm^3$) and a gas contact area of 38 ($cm^2$), while the drain separator a2 has an internal volume of 11.0 ($cm^3$) and a gas contact area of 50 ($cm^2$).

As shown in FIG. 3, the drain separator b includes a separation section made of glass and formed in a spherical shape having a large diameter to condense the moisture in a sample gas as a condensed water and separating the condensed water from the sample gas, and a fan (not shown) serving as cooling means. The drain separator b has an internal volume of 270.0 ($cm^3$) and a gas contact area of 200 ($cm^2$). The drain separator c includes a separation section made of PVC and formed in a cylindrical shape having a large diameter to condense the moisture in a sample gas as a condensed water and separating the condensed water from the sample gas, without cooling means, as shown in FIG. 3. The drain separator c has an internal volume of 320.0 ($cm^3$) and a gas contact area of 280 ($cm^2$).

Table 1 shows the result of the experimental test of the $NO_2$ loss performed by passing 2000 ($cm^3$/min) of sample gas through each of the four different drain separators a1, a2, b, c.

TABLE 1

| Component Name and Characteristic of Form/ Factorial Parameter | Spiral type Cooling Tube a1 | Spiral type Cooling Tube a2 | Glass Drain Separator b | PCV Drain Separator c |
|---|---|---|---|---|
| $NO_2$ Loss (%) | 0.46 | 1.20 | 2.09 | 3.42 |
| Gas Contact Area (Internal Surface Area) S ($cm^2$) | 38 | 50 | 200 | 280 |
| Volume V ($cm^3$) | 5.6 | 11 | 270 | 320 |
| Flow Rate L ($cm^3$/min) | 2,000 | 2,000 | 2,000 | 2,000 |
| Flow Rate-Volume Ratio (Flow Rate/Volume) L/V ($min^{-1}$) | 357.1 | 181.8 | 7.4 | 6.3 |
| Flow Rate-Internal Surface Area Ratio (Flow Rate/Internal Surface Area) L/S (cm/min) | 52.6 | 40 | 10 | 7.1 |

As seen in Table 1, the high-flow-velocity cooling type drain separators a1, a2 as used in this embodiment exhibit lower $NO_2$ losses than those of the conventional drain separators c, b.

For each of the drain separators a1, a2, b, c, Table 1 shows a ratio of the flow rate of a sample gas passing through the drain separator to the internal volume of the drain separator (hereinafter referred to as "flow rate-volume ratio"), and a ratio of the flow rate of the sample gas passing through the drain separator to the internal surface area (gas contact area) of a sample gas passage formed in the drain separator (hereinafter referred to as "flow rate-interior surface area ratio"). The flow rate-volume ratios of the drain separators a1, a2, b and c are 357.1 ($min^{-1}$), 181.8 ($min^{-1}$), 7.4 ($min^{-1}$) and 6.3 ($min^{-1}$), respectively. The flow rate-interior surface area ratios of the drain separators a1, a2, b and c are 52.6 (cm/min), 40 (cm/min), 10 (cm/min) and 7.1 (cm/min), respectively.

Figure 4:
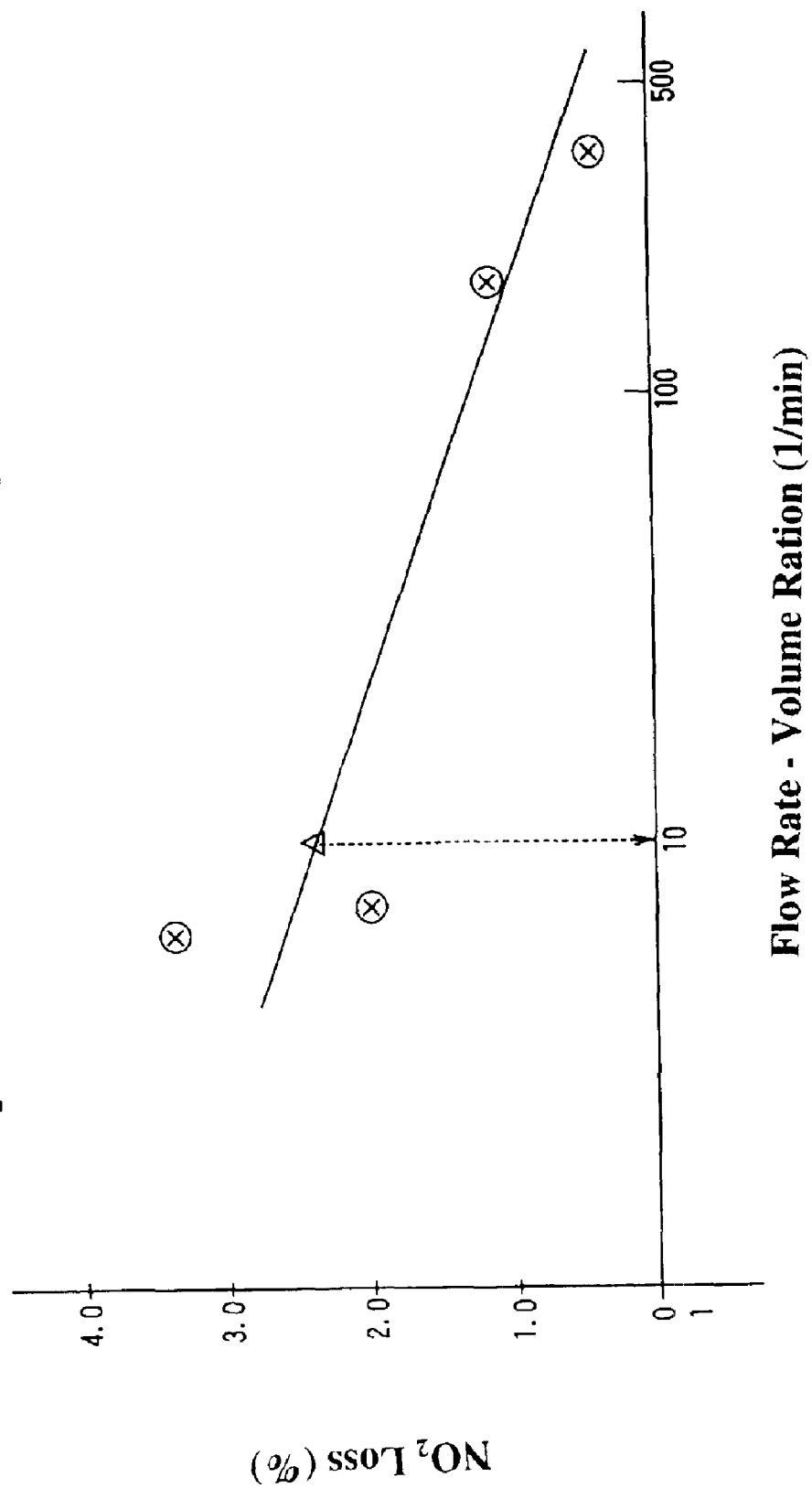
FIG. 4 is a schematic graph showing the relationship between an $NO_2$ loss and a flow rate to internal volume ratio.

FIG. 4 shows a graph having a horizontal axis representing each of the flow rate-volume ratios of the drain separators a1, a2, b, c and a vertical axis representing each of the $NO_2$ losses of the drain separators a1, a2, b, c. The graph in FIG. 4 shows the relationship between the flow rate-volume ratio and the $NO_2$ loss. As seen in this graph, the $NO_2$ loss is reduced as the flow rate-volume ratio is increased, and it is required to set the flow rate-volume ratio at 10 ($min^{-1}$) or more so as to achieve a desirably reduced $NO_2$ loss of 2.5% or less.

Figure 5:
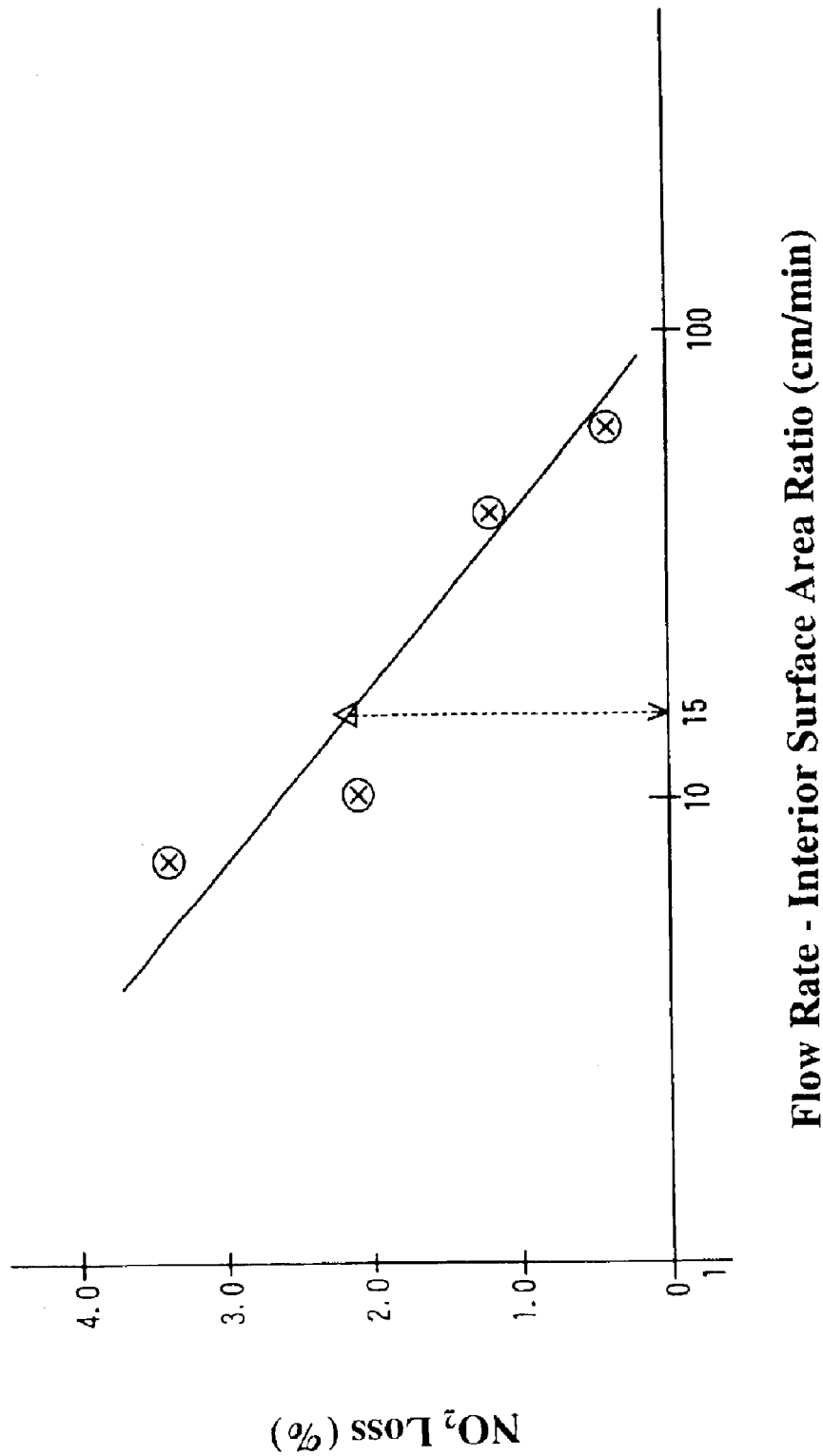
FIG. 5 is a schematic graph showing the relationship between an $NO_2$ loss and a flow rate to internal surface area ratio.

FIG. 5 shows a graph having a horizontal axis representing each of flow rate-interior surface area ratios of the drain separators a1, a2, b, c and a vertical axis representing each of the $NO_2$ losses of the drain separators a1, a2, b, c. The graph in FIG. 5 shows the relationship between the flow rate interior surface area ratio and the $NO_2$ loss. As seen in this graph, the $NO_2$ loss is reduced as the flow rate interior surface area ratio is increased, and it is required to set the flow rate interior surface area ratio at 15 ($min^{-1}$) or more so as to achieve the desirably reduced $NO_2$ loss of 2.5% or less.

The respective relationships between the flow rate volume ratio and the $NO_2$ loss and between the flow rate interior surface area ratio and the $NO_2$ loss are also subject to the type or specifications of drain separator and/or a sample gas to be used. Thus, the plots on the graph for the different drain separators a1, a2, b, c have a certain level of dispersion.

Figure 6:
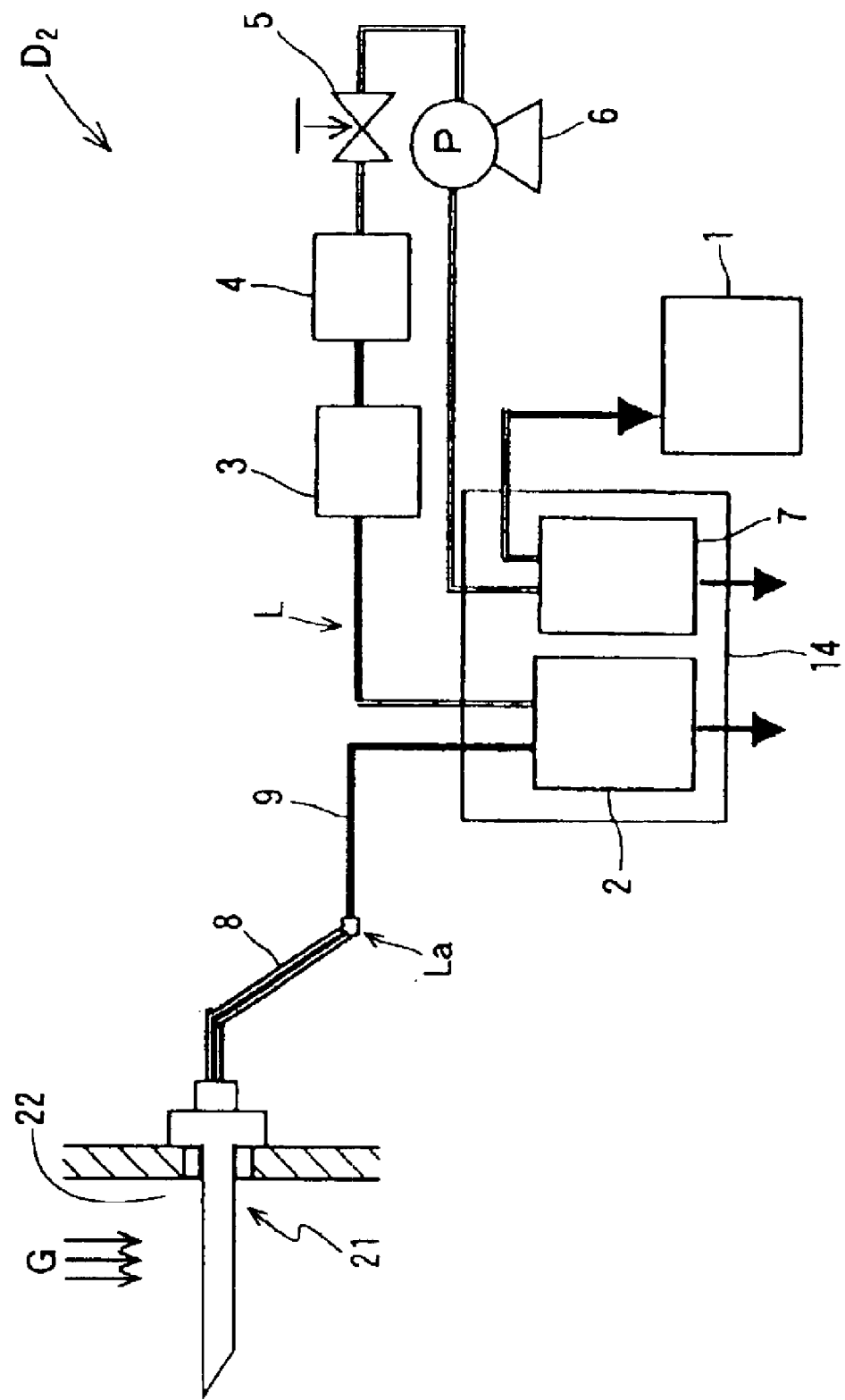
FIG. 6 is a schematic explanatory block diagram showing a NOx-concentration measuring apparatus according to a second embodiment of the present invention.

FIG. 6 is a schematic explanatory block diagram showing a NOx-concentration measuring apparatus D2 according to a second embodiment of the present invention. In FIG. 6, the same components or elements as those in the first embodiment are represented by the same reference numerals or codes, and their description will be omitted.

The measuring apparatus D2 is different from the measuring apparatus D of the first embodiment in that both the drain separator 2 and the secondary cooling device 7 are incorporated in a single unit.

Figure 7:
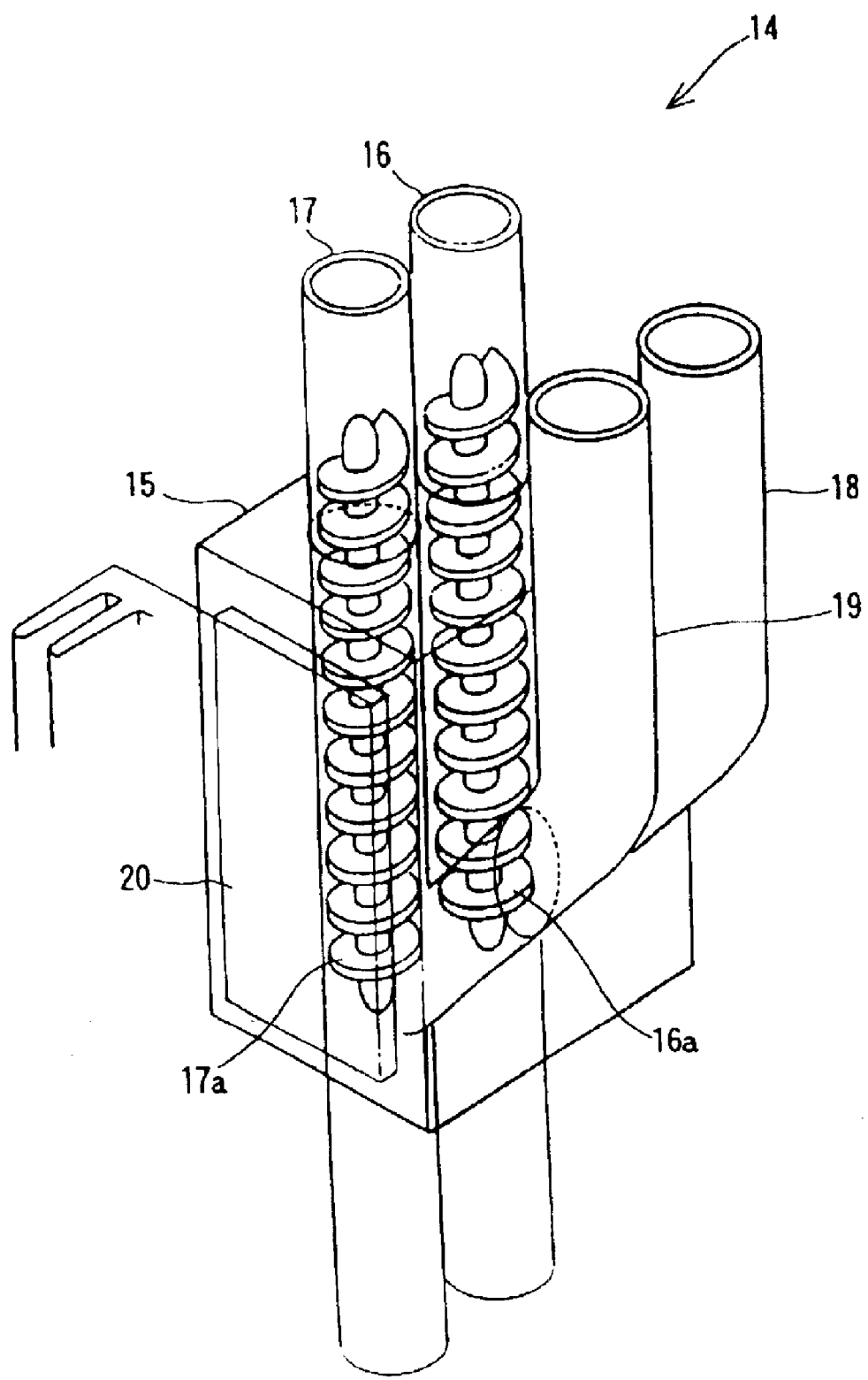
FIG. 7 is a schematic fragmentary perspective view showing a dual-drain cooling device in the second embodiment.

More specifically, the drain separator 2 and the secondary cooling device 7 are incorporated in a dual-drain cooling device 14. As shown in FIG. 7, the dual-drain cooling device 14 comprises a block 15 made of a metal having a high thermal conductivity, a pair of heat exchange pipes 16, 17 extending penetratingly through the block 15 approximately vertically and approximately in parallel with one another, a first branch passage 18 branched from the heat exchange pipe 16 to extend obliquely upward, a second branch passage 19 branched from the heat exchange pipe 17 to extend obliquely upward, and cooling means 20 for cooling the block 15.

The block 15 may be formed in an approximately rectangular parallelepiped or cubic shape.

The first heat exchange pipe 16 has an approximately circular cross-section, and includes a first spiral-channel forming member 16a for forming a spiral channel mainly in a portion of the first heat exchange pipe 16 located inside the block 15. The first spiral-channel forming member 16a may also be made a metal having a high thermal conductivity.

The second heat exchange pipe 17 has an approximately circular cross-section, and includes a second spiral-channel forming member 17a for forming a spiral channel mainly in a portion of the second heat exchange pipe 17 located inside the block 15. The second spiral-channel forming member 17a may also be made a metal having a high thermal conductivity.

The first branch passage 18 is branched from the lower portion of the first heat exchange pipe 16 located inside the block 15.

The second branch passage 19 is branched from the lower portion of the second heat exchange pipe 17 located inside the block 15.

The cooling means 20 is fixed onto and along one of the side surfaces of the block 15. The cooling means 20 may be formed by use of a thermoelectric-cooling Peltier element (Peltier cooling element). Further, the heat exchange pipe 17 is disposed closer to the side surface of the block 15 having the cooling means 20 fixed thereto than the first heat exchange pipe 16. Thus, the interior of the second heat exchange pipe 17 is cooled down to a lower temperature than that of the interior of the first heat exchange pipe 16.

In the dual-drain cooling device 14 constructed as above, the drain separator 2 is composed of the block 15, the first heat exchange pipe 16, the first branch passage 18 and the cooling means 20, while the secondary cooling device 7 is composed of the block 15, the second heat exchange pipe 17, the second branch passage 19 and the cooling means 20. Further, a sample gas can be additionally cooled by the secondary cooling device 7 by disposing the second heat exchange pipe 17 closer to the cooling means 20 than the first heat exchange pipe 16 of the drain separator 2.

Operation of the drain separator 2 and the secondary cooling device 7 constricted as above are the same as that of the drain separator 2 in the first embodiment, and its description will be omitted.

Immediately after the sample gas, supplied from the introduction line La at about 65° C., gets out of the drain separator 2 through the first heat exchange pipe 16 and the first branch passage 18, its temperature will be about 5° C. lower than room temperature. Thus, the moisture contained in the sample gas is eliminated or condensed until reaching a saturation point at the above temperature, and the condensed water is then discharged from the drain separator 2 together with $NH_3$ dissolving in the condensed water. Further, immediately after the sample gas, supplied through the $NO_2$ converter 4, gets out of the secondary cooling device 7 through the second heat exchange pipe 17 and the second branch passage 19, its temperature will be about 2.5 to 5° C.

In the measuring apparatus D2 constructed as above, the drain separator 2 and the secondary cooling device 7 can be advantageously incorporated in a single unit to provide a structurally simplified and downsized apparatus, in addition to the advantages in the measuring apparatus D according to the first embodiment.

As mentioned above, the present invention can provide a NOx-concentration measuring apparatus capable of suppressing $NO_2$ loss due to adsorption and/or dissolution of $NO_2$ to provide a high-precision measurement.

What is claimed is:

1. A NOx-concentration measuring apparatus for quantitatively analyzing the concentration of NOx contained in a sample gas, comprising:
    a sampling probe for obtaining the sample gas;
    a drain separator for condensing moisture contained in the sample gas as a condensed water and separating the condensed water from the sample gas, said drain separator having a cooling device therein for cooling the sample gas;
    an $NO_2$ converter for converting $NO_2$ contained in the sample gas into NO;
    a secondary cooling device for additionally cooling the sample gas; and
    an NO analyzer, arranged in above stated order with respect to a sample-gas line of said NOx-concentration measuring apparatus,
    wherein said drain separator is operable to cool the sample gas passing therethrough at a high flow velocity such that a ratio of the flow rate ($cm^3$/min) of said sample gas passing through said drain separator to the internal volume ($cm^3$) of said drain separator is set at 10 ($min^{-1}$) or more; and
    the sample-gas line between said sampling probe and said drain separator is heated and/or thermally insulated over the entire length thereof.

2. A NOx-concentration measuring apparatus for quantitatively analyzing the concentration of NOx contained in a sample gas, comprising:
    a sampling probe for obtaining the sample gas;
    a drain separator for condensing moisture contained in the sample gas as a condensed water and separating the condensed water from the sample gas, said drain separator having a cooling device therein for cooling the sample gas;
    an $NO_2$ converter for converting $NO_2$ contained in the sample gas into NO;
    a secondary cooling device for additionally cooling the sample gas; and
    an NO analyzer, arranged in above stated order with respect to a sample-gas line of said NOx-concentration measuring apparatus,
    wherein said drain separator is provided with a sample-gas passage serving as a part of said sample-gas line,
    a ratio of the flow rate ($cm^3$/min) of the sample gas passing through said drain separator to the internal surface area ($cm^2$) of said sample-gas passage is set at 15 (cm/min) or more, and
    the sample-gas line between said sampling probe and said drain separator is heated and/or thermally insulated over the entire length thereof.

3. A NOx-concentration measuring apparatus for quantitatively analyzing the concentration of NOx contained in a sample gas, comprising:
    a sampling probe for obtaining the sample gas;
    a drain separator for condensing moisture contained in the sample gas as a condensed water and separating the condensed water from the sample gas, said drain separator having a cooling device for cooling the sample gas;
    an $NO_2$ converter for converting $NO_2$ contained in the sample gas into NO;
    a secondary cooling device for additionally cooling the sample gas; and
    an NO analyzer, arranged in above stated order with respect to a sample-gas line of said NOx-concentration measuring apparatus,
    wherein said drain separator is operable to cool the sample gas passing through a sample-gas passage, formed therein to serve as a part of said sample-gas line, at a high flow velocity such that a ratio of the flow rate ($cm^3$/min) of said sample gas passing through said drain separator to the internal volume ($cm^3$) of said drain separator is set at 10 ($min^{-1}$) or more, and a ratio of the flow rate ($cm^3$/min) of said sample gas passing through said drain separator to the internal surface area ($cm^2$) of said sample-gas passage is set at 15 (cm/min) or more, and
    the sample-gas line between said sampling probe and said drain separator is heated and/or thermally insulated over the entire length thereof.

4. The NOx-concentration measuring apparatus as defined in claim 1, wherein said drain separator and said secondary cooling device are incorporated in a single unit.

5. The NOx-concentration measuring apparatus as defined in claim 2, wherein said drain separator and said secondary cooling device are incorporated in a single unit.

6. The NOx-concentration measuring apparatus as defined in claim 3, wherein said drain separator and said secondary cooling device are incorporated in a single unit.

* * * * *